United States Patent [19]
Mikecz et al.

[11] Patent Number: 6,001,356
[45] Date of Patent: *Dec. 14, 1999

[54] METHOD OF INHIBITING TISSUE DESTRUCTION IN AUTOIMMUNE DISEASE USING ANTI-CD44 ANTIBODIES

[75] Inventors: Katalin Mikecz; Tibor Tivadar Glant, both of Oak Park, Ill.

[73] Assignee: Rush-Presbyterian-St. Luke's Medical Center, Chicago, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/721,118

[22] Filed: Sep. 26, 1996

Related U.S. Application Data
[60] Provisional application No. 60/004,627, Sep. 29, 1995.

[51] Int. Cl.⁶ .................................................. A61K 39/395
[52] U.S. Cl. ..................... 424/144.1; 424/130.1; 424/133.1; 424/141.1; 424/143.1; 424/152.1; 424/153.1; 424/154.1; 424/172.1; 424/173.1
[58] Field of Search .............................. 424/133.1, 141.1, 424/130.1, 143.1, 152.1, 172.1; 530/387.1, 388.1, 388.7

[56] References Cited

U.S. PATENT DOCUMENTS

| | | | |
|---|---|---|---|
| 4,550,086 | 10/1985 | Reinherz et al. | 436/506 |
| 4,695,459 | 9/1987 | Steinman et al. | 424/95 |
| 4,840,793 | 6/1989 | Todd, III et al. | 424/85.8 |
| 4,935,234 | 6/1990 | Todd, III et al. | 424/85.8 |
| 5,002,869 | 3/1991 | Schlossman et al. | 435/7.24 |
| 5,019,648 | 5/1991 | Schlossman et al. | 530/387 |
| 5,147,637 | 9/1992 | Wright et al. | 424/85.8 |
| 5,216,131 | 6/1993 | Lasky et al. | 530/350 |
| 5,284,931 | 2/1994 | Springer et al. | 424/85.8 |
| 5,288,854 | 2/1994 | Diamond et al. | 530/395 |
| 5,318,890 | 6/1994 | Rosen et al. | 435/7.24 |
| 5,324,510 | 6/1994 | Wegner et al. | 424/85.8 |
| 5,378,464 | 1/1995 | McEver et al. | 424/143.1 |
| 5,403,713 | 4/1995 | Bevilacqua et al. | 435/7.1 |
| 5,403,919 | 4/1995 | Butcher | 530/388.2 |
| 5,426,029 | 6/1995 | Rittershaus et al. | 435/7.21 |
| 5,504,194 | 4/1996 | St. John et al. | 530/395 |

FOREIGN PATENT DOCUMENTS

| | | |
|---|---|---|
| 0501233 | 9/1992 | Austria . |
| 303463 | 2/1989 | Germany . |
| 9409811 | 5/1994 | WIPO . |

OTHER PUBLICATIONS

Camp et al. J Exp Med. 178: 497–507 (1993).
Bazil et al. J. Immunol. 149: 747–753 (1992).
Verdrengh et al (1995) Scand. J. Immunol. 42:353–58.
Brennan et al. Arthritis & Rheumatism 38(9 Suppl) S280, # 793 (1995).
Aruffo et al., "CD44 Is the Principal Cell Surface Receptor for Hyaluronate," *Cell*, vol. 61, pp. 1303–1313 (1990).
Lesley et al., "CD44 and Its Interaction with Extracellular Matrix," *Advances in Immunology*, vol. 54, pp. 271–335 (1993).
Mikecz et al., "Immunotherapy with Antibodies to Cell Adhesion Molecules in Proteoglycan–Induced Arthritis," Abstract for the 58th Annual Scientific Meeting of the American College of Rheumatology, Oct. 1994. Arthritis Rheum 37(9) Suppl p. S191 (1994).
Mickecz et al., "Anti–CD44 Treatment Abrogates Tissue Oedema and Leukocyte Infiltration in Murine Arthritis," *Nature Medicine*, 1(6): 558–563 (1995).

*Primary Examiner*—Christina Y. Chan
*Assistant Examiner*—Phillip Gambel
*Attorney, Agent, or Firm*—Fitch, Even, Tabin & Flannery

[57] ABSTRACT

The present invention provides a method for preventing tissue destruction associated with autoimmune inflammatory diseases by utilizing anti-CD44 monoclonal antibodies to induce the loss of the CD44 receptor from cell surfaces, thus preventing the interaction between cell-surface CD44 and extracellular hyaluronan.

8 Claims, 3 Drawing Sheets

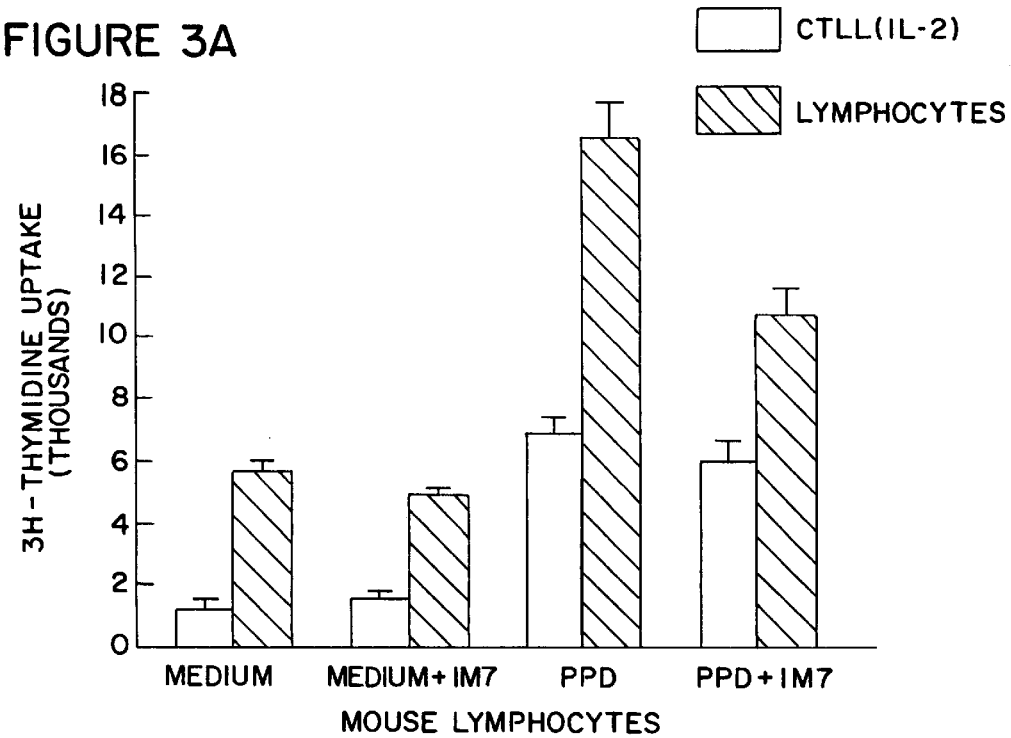
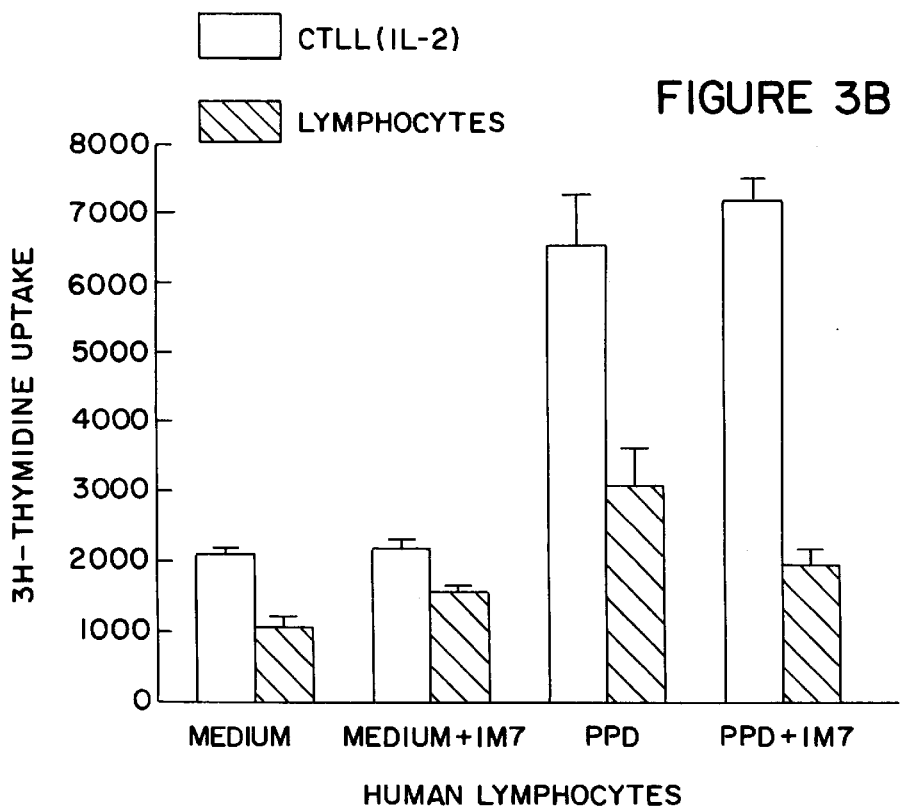

METHOD OF INHIBITING TISSUE DESTRUCTION IN AUTOIMMUNE DISEASE USING ANTI-CD44 ANTIBODIES

This application claims benefit of U.S. Provisional Application No. 60/004,627, filed Sep. 29, 1995.

FIELD OF THE INVENTION

The present invention relates to a method for preventing the tissue destruction associated with autoimmune inflammatory diseases. More particularly, the invention provides a method of using anti-CD44 antibodies to induce the loss of CD44 receptors from cell surfaces and prevent binding of extracellular hyaluronan to cells.

BACKGROUND OF THE INVENTION

The ability to control inflammatory and immune responses is central to the therapy of a wide spectrum of diseases. General anti-inflammatory agents (corticosteroids and non steroidal anti-inflammatory drugs, i.e. NSAIDs, such as aspirin) acting to suppress or regulate immune-mediated reactions throughout the body, are widely used in this context. The modulation of receptors and various functions of leukocytes which participate in, and are responsible for, the local response of the injured tissue, illustrates a new approach in clinical patient care. Biological agents, such as antibodies directed to inflammatory leukocytes or their receptors, provide important control mechanisms through which immune-mediated tissue destruction can be prevented.

Specific receptors with binding affinity for a variety of ligands are found on the surface of cells that participate in the inflammatory response. CD44 (also referred to as PgP-1, phagocytic glycoprotein-1) is a cell adhesion receptor which preferentially binds hyaluronan (Aruffo et al., Cell, 61 (1990) 1303–1313). CD44 is expressed by many cell types (Lesley et al., Adv. in Immunol., 54 (1993) 271–335) and expressed in high levels by synovial cells and leukocytes during joint inflammation (Haynes et al., Arthritis Rheum., 34 (1991) 1434–1443; Mikecz et al., Scand. Rheumatol., 101 (1994) 91–98). The CD44 glycoprotein is expressed in several isoforms as a result of differential splicing (Gunthert et al., Curr Topics Microbiol. Immun., 184 (1993) 47–63; Gunthert et al., Cell, 65 (1991) 13–24; MacKay et al., J.Cell Biol., 124 (1994) 71–82).

Leukocytes responsible for immune-mediated tissue injury, and cells residing in the tissue and extracellular matrix function together to effect an inflammatory response. The extracellular matrix (ECM) fills the space between cells. Although it has long been recognized that the components of the ECM perform an important structural role, it has been realized more recently that the ECM communicates with the cell interior and thus modulates cell adhesion, proliferation, and differentiation (Schubert, Trends Cell Biol., 2 (1992) 63–66). Major constituents of the ECM include collagenous proteins (Linsenmayer, Cell Biology of the Extracellular Matrix, Plenum, N.Y. (1991) 7–44) and proteoglycans. The latter consist of one or more glycosaminoglycans, which are linear polymers of repeating disaccharides covalently bound to a protean core. Hyaluronan (hyaluronic acid, hyaluronate), a glycosaminoglycan macromolecule without a protein core, is one of the major non-structural elements of the extracellular matrix (Laurent et al., FASEB J., 6 (1992) 2397–2404; Aruffo et al., Cell, 61 (1990) 1303–1313; Culty et al., J. Cell Biol., 111 (1990) 2765–2774; Underhill, J. Cell Sci., 103 (1992) 293–298; Toole, Cell Biology of Extracellular Matrix, (1991) Plenum, N.Y.).

The biological roles of hyaluronan include the maintenance of water and protein homeostasis as well as the protection of cells from potentially harmful effects of other cells, microorganisms and macromolecules. To gain access to cells surrounded by hyaluronan-rich matrices, some cells and bacteria use hyaluronidase. Other cells utilize hyaluronan binding receptors such as CD44 (Laurent et al., FASEB J., 6 (1992) 2397–2404; Toole, Cell Biology of Extracellular Matrix, (1991) Plenum, N.Y.; Lesley et al., Exp. Cell Res., 187 (1990) 224–233; Bartolazzi et al., J. Exp. Med., 180 (1994) 53–66; Thomas et al., J. Cell Biol., 118 (1992) 971–977; Herrlich et al., Immun. Today, 14 (1993) 395–399). The interaction of CD44 with hyaluronan facilitates the migration of these cells within the extracellular matrix. Further, hyaluronan molecules have large hydrodynamic volumes that entrap substantial amounts of water and can, hence, control tissue hydration (swelling).

Lymphocytes acquire enhanced binding affinity toward hyaluronan upon activation (Stamenkovic et al., Embo J., 10 (1991) 343–348; Hathcock et al., J. Immun., 151 (1993) 6712–6722). Hyaluronan-binding splice variants of CD44 confer metastatic proclivity to malignant cells (Gunthert et al., Cell, 65 (1991) 13–24). Recombinant CD44H (hemopoietic form) proteins and antibodies that recognize CD44H inhibit both cell adhesion to hyaluronan and migration of cells on hyaluronan-coated surfaces. Taken together, these findings suggest an important role for the CD44-hyaluronan interaction during physiological and pathological events in which cell migration within the ertracellular space is involved.

Researchers have attempted to modulate the immune response by developing antibodies to specific receptors and hence prevent binding of any other ligand to that receptor. A number of patents describe antibodies directed to various adhesion associated molecules. For example, U.S. Pat. No. 5,147,637 describes a method of inhibiting the influx of leukocytes into the lung and other organs during sepsis or other infectious or non-infectious trauma by administering a therapeutic amount of and anti-CD18 antibody. U.S. Pat. No. 4,695,459 describes a method of treating autoimmune disease, such as multiple sclerosis, rheumatoid arthritis and systemic lupus erythematosus by administering a therapeutically effective amount of anti-Leu3 antibody to the patient, which would eliminate T lymphocytes. Further, U.S. Pat. No. 5,019,648 describes the use of anti-CD11b antibodies to inhibit adhesion dependent functions of phagocytic cells. None of these patents describe CD44 receptor, its interaction with hyaluronan or a method wherein antibody binding results in the loss of receptors from the cell surface.

Methods have been described for the therapeutic use of antibodies to prevent leukocyte extravasation in individuals having autoimmune diseases such as rheumatoid arthritis. For example, U.S. Pat. No. 5,216,131 describes the therapeutic use of lymphocyte homing receptor protein (LHR) to compete with the normal binding of lymphocytes to lymphoid tissue for the treatment of patients with inflammations due to rheumatoid arthritis or other autoimmune diseases. European Patent Application 303,463 and corresponding U.S. Pat. No. 5,403,919 describe antibodies having recognition for a 58–69 kD mouse endothelial cell surface antigen present on the surface of high endothelial venule (HEV) cells in all lymphoid organs, and a 85–95 kD synovial-specific leukocyte glycoprotein which is a homing receptor for synovial endothelium. The antibodies having recognition for these endothelial cells surface antigens are capable of inhibiting the binding of leukocytes to endothelial cells, thereby inhibiting lymphocyte extravasation via such endothelial cells in vivo.

The antigens described in 5,216,131 and EP 303,463 are structurally and functionally different from CD44. CD44 is not a homing receptor as none of the isoforms of CD44 contain binding sites for endothelial cell-membrane carbohydrates which are commonly recognized by homing receptors, and anti-CD44 antibodies do not disturb normal lymphocyte homing in vivo (Camp et al., *J. Exp. Med.*, 178 (1993) 497–507; Mikecz et al., *Nature Med.*, 1 (1995) 558–563). Further, CD44 is the principal receptor for hyaluronan, which is a component of extracellular or pericellular matrix, and the digestion of lymphoid tissues with hyaluronidase eliminates CD44 binding. Thus, CD44-bearing leukocytes do not recognize endothelial cells directly in either the lymph node or synovial tissue. Leukocyte CD44, however, can bind hyaluronan, which is not an integral part of the endothelial cell, but may be present in the extra- or pericellular matrix around the endothelium, especially in inflamed tissue where hyaluronan is abundantly produced.

CD44 is not synovial specific leukocyte glycoprotein as it has been shown to be expressed in many cell types besides leukocytes (Lesley et al., *Adv. in Immunol.*, 54 (1993) 271–335; Mikecz et al., *Scand. J. Rheumatol.*, 101 (1994) 91–98). EP 303,4463 describes antibodies which are able to inhibit leukocyte binding to the endothelium of target organs by blocking leukocyte-endothelial cell recognition, i.e. the antibodies block cell-cell contact but not hyaluronan-cell interaction. Hence, none of the references describe an antibody having a twofold anti-inflammatory effect provided by binding CD44 receptors on connective tissue cells and leukocyte CD44 receptors such that receptors are lost from the cell surface, hyaluronan binding and associated swelling is reduced, and leukocyte migration is inhibited.

It is thus an object of the present invention to provide an immunotherapeutic method for the treatment of humans or animals to control autoimmune inflammatory diseases.

Another object of the invention is to provide a therapeutic regimen which provides the maximal desired anti-inflammatory effect balanced with the least adverse side effects.

Yet another object of the invention is to provide an immunotherapeutic method wherein antibodies to CD44 receptors are utilized to inhibit the interaction of CD44 receptors with hyaluronan such that tissue swelling is reduced and leukocyte extravasation is inhibited.

It is an additional object of the invention to provide a method wherein the binding of antibodies to CD44 results in the loss of CD44 receptor from the surface of the cell.

SUMMARY OF THE INVENTION

The present invention provides a method for inhibiting tissue destruction associated with autoimmune inflammatory diseases by utilizing anti-CD44 therapy. According to the method of the invention, antibody to CD44 is administered in an amount effective for inducing the loss of the CD44 receptor from the cell surface, thus preventing the interaction between cell-surface CD44 and hyaluronan.

CD44 receptors are essential for leukocytes to recognize inflammatory sites distinctly, and hyaluronan may facilitate the transendothelial migration of these cells. Once the leukocytes pass through the endothelial barrier, the oedematous expansion of the extracellular space allows CD44 leukocytes to move among connective tissue cells, and along a hyaluronan network. Anti-CD44 antibody IM7 acts to inhibit the formation of hyaluronan-rich pericellular matrix around synovial cells in vitro and rapidly reduces joint oedema in vivo, thus inhibiting the accumulation of hyaluronan and hyaluronan-bound water in the extracellular matrix. Simultaneously, binding of antibody IM7 to CD44 induces the loss of CD44 from the surface of leukocytes, rendering these cells unable to recognize hyaluronan. Therefore, leukocytes lose their ability to migrate into the inflamed tissue. Thus, the powerful anti-inflammatory effect of anti-CD44 treatment lies in its twofold action exerted on both CD44-expressing connective tissue cells and leukocytes. Both cell types share common hyaluronan recognition motifs of CD44 and an enhanced affinity toward this polysaccharide at the site of inflammation.

Other objects, advantages, features and characteristics of the present invention will become more apparent upon consideration of the following description and the appended claims.

Figure 1A:
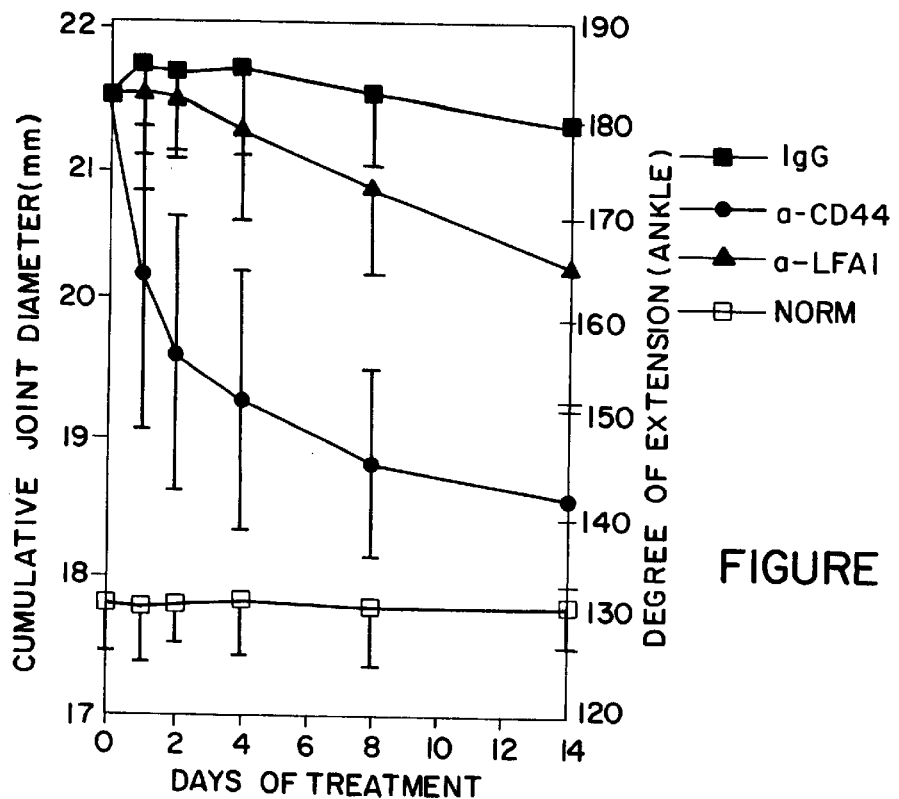
FIGS. 1A-B describes the effects of treatment with anti-CD44 antibody IM7 and anti-CD18 antibody M18 on tissue swelling (FIG. 1A) and joint deformities (FIG. 1B) in mice with acute experimental polyarthritis. Open squares represent the baseline values measured in normal (untreated) non-arthritic mice (n=15), solid squares show the values of rat IgG-injected arthritic animals (n=18); solid circles, arthritic mice treated with anti-CD44 antibody IM7 (n=18); and solid triangles, arthritic animals injected with anti-CD18 antibody M18 (n=15). The standard errors of measurement are represented by the error bars. Since BALB/c mice with proteoglycan-induced and DBA/1 mice with collagen-induced arthritis produced identical results, both are included in the measurements. Joint swelling (FIG. 1A) is expressed as the cumulative joint diameter of the wrist and ankle joints measured in both frontal and sagittal directions. There was a statistically significant decrease in joint swelling ($P<0.05$) in IM7-treated animals by day 1, and the cumulative joint diameters remained significantly lower ($P<0.05$) from day 2 through day 14 than those of mice injected with either rat IgG or monoclonal antibody M18 (note that the Repeated Measures Analysis of Variance test maintains one selected ($P<0.05$) P value throughout the multiple-range analysis of the data). The degree of extension (FIG. 1B) refers to the angles measured in ankle joints (maximum extension of 180° was measured in non-arthritic mice). Extension was already reduced in the swollen joints of all arthritic animals (day 0 of treatment). Statistical analyses showed that the extension had decreased significantly in IgG- and M18-treated animals by day 14, as compared with monoclonal antibody IM7-injected mice, which developed only mild deformities in the ankle joints. Arthritic mice treated with monoclonal antibody M18 showed a significant decrease in joint swelling (FIG. 1A) by day 8 and improvement in ankle extension (FIG. 1B) by day 14 as compared with IgG-injected animals. However, the overall clinical improvement in these mice was slower and less impressive than in IM7-injected animals. Injection of arthritic mice with either rat IgG or irrelevant rat monoclonal antibodies (IgG2a (n=9) and IgG2b (n=10)) or PBS (n=10), produced identical results (data not shown).

(black bars). Low numbers of CD44+ cells were detected by flow cytometry on PBLs of normal donors and on RA fibroblasts, while no CD44+ cells remained among RA PBLs and RA-SFLs following a 6 hour incubation with IM7. PBLs of RA patients #1 and #4 bound hyaluronan from medium, which was removed by hyaluronidase (Hy) treatment. Immunostaining was performed with anti-human CD44 mAb A3D8 which recognizes the HA-binding region of CD44 and interferes with HA but not with IM7 binding. The y axis represents the percentage of cells immunostained with mAb A3D8.

FIGS. 3A-B illustrates that treatment of mouse (FIG. 3A) or human (FIG. 3B) lymphocytes with mAb IM7 in vitro does not affect the immunologic reaction (interleukin-2 production) of T lymphocytes, but slightly reduces proliferative response to the recall antigen PPD. Mouse (FIG. 3A) or human (FIG. 3B) lymphocytes were cultured with PPD in the presence or absence of mAb IM7. The standard errors of measurement are represented by the error bars. Interleukin-2 content of the supernatant was measured by $^3$H-thymidine incorporation of interleukin-2 sensitive CTLL cells (black bars), and lymphocyte blast transformation/proliferation by $^3$H-thymidine uptake by the cultured lymphocytes themselves (shaded bars). PPD is a purified protein derivative of *Mycobacterium tuberculosis* to which both immunized mice and BCG-vaccinated humans are sensitive. The bacillus Calmette-Guerin (BCG) is an attenuated Mycobacterium strain used to immunize humans against tuberculosis.

DETAILED DESCRIPTION OF THE INVENTION

Definitions

The following definitions are provided in order to provide clarity as to the intent or scope of their usage in the specification and claims. All patents and publications referred to herein are incorporated by reference herein. "Inflammation" and "inflammatory reaction" refer to the local response of a tissue to infection or immune-mediated injury caused by the invasion of white blood cells (leukocytes) which release various mediators such as histamine, interleukins and prostaglandins. Characteristic symptoms of inflammation include redness, swelling, heat, pain and loss of tissue function.

"Antibody" refers to a member of a family of glycosylated proteins called immunoglobulins, which can specifically combine with an antigen. The term is intended to include all classes of immunoglobulins (IgG, IgM, IgA, IgD, or IgE) and antigen binding fragments (e.g., Fab, F(ab')$_2$, Fab') as well as whole immunoglobulins.

The term "monoclonal antibody" means an antibody population having a homogenous antibody composition, each number of which binds to the same antigenic determinant(s).

"Antigen" refers to a protein or synthetic peptide compound which will produce antibody formation without chemical modification. More particularly, the term refers to a CD44 receptor.

"Leukocytes" are white blood cells which include granulocytes, monocytes, and lymphocytes.

The term "autoimmune disease" refers to a condition where tissue injury is caused by an immunologic reaction of the host with its own tissues. Examples of some autoimmune diseases and related disorders are listed in Table I.

TABLE I

Autoimmune and Related Disorders

Systemic Lupus Erythematosus
Rheumatoid Arthritis
Polyarteritis Nodosa
Polymyositis and Dermatomyositis
Progressive Systemic Sclerosis (Diffuse Scleroderma)
Glomerulonephritis
Myasthenia Gravis
Sjogren's Syndrome
Hashimoto's Disease and Graves' Disease
Autoimmune adrenalitis (Addison's Disease)
Type I Diabetes Mellitus
Multiple Sclerosis and Related Demyelinating Diseases
Uveitis
Pemphigus and Pemphigoid
Ulcerative Colitis
Rheumatic Carditis "Rheumatoid arthritis" is a destructive inflammatory disease involving primarily the joints of extremities. The disease is characterized by inflammation of the synovium and destruction of the joint cartilage, with a pathologic picture suggestive of local autoimmune reactions.

"Experimental models of autoimmune diseases" are produced by immunizing animals with various antigens. Some of these diseases may develop spontaneously in certain species and strains of animals at old age. The immune responses cause organ-specific inflammation and tissue destruction which resemble human autoimmune disorders. For example, in certain strains of rats and mice, immunization with cartilage collagen, proteoglycan or Freund's complete adjuvant induces joint inflammation similar to that seen in rheumatoid arthritis.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient. Pharmaceutical compositions comprising inhibitors of receptor binding can be used to block or inhibit cellular adhesion associated with a number of disorders. For instance, a number of inflammatory disorders are associated with receptors expressed on vascular endothelial cells and leukocytes.

PREPARATION OF ANTIBODY

The general procedure for making monoclonal antibodies by hybridoma technology is well known, and the procedure used for producing monoclonal antibodies (mAbs), specifically anti-CD44 antibody IM7, is described in detail in Example 1. Originally, the mAb TM7 was generated using a myeloid cell line from mouse bone marrow for the immunization of rats (Trowbridge et al., *Immunogenetics*, 15 (1982) 299–312). The hybridoma is available commercially from American Type Culture Collection as "Rat hybridoma, clone IM7.8.1, producing anti-mouse Pgp-1 mAB".

Briefly, the processes for producing monoclonal antibodies involve fusing myeloma cells and lymphocytes by using a fusogen, typically polyethylene glycol. Myeloma cell lines that may be used in the process are known and available. The lymphocytes, typically either spleen cells or B cells, are obtained from mice or rats immunized with crude stromal preparations of particular organs or tissues, or states of tissue (e.g., lymph node stroma, synovial stroma, or stroma of any other lymphoid or inflamed tissue) or with isolated cells from such tissues. The fused cells or hybridomas are then expanded in a nutrient medium containing hypoxanthine, aminopterin, and thymidine (HAT). The cells surviving the incubation are assayed for production of the desired antibody and positive cells are sorted and cloned by known techniques. Following production of hybridomas, supernatants are screened for relevant antibodies by immunohistology and in animal models. The monoclonal antibodies expressed by the clones may be harvested and purified by known techniques.

Although xenogeneic antibodies may be used in the invention, one could also use allogeneic or hybrid antibodies to reduce the likelihood of the antibodies themselves inducing an immune response from the host. An allogeneic monoclonal antibody is one that is expressed by a hybridoma made by fusing cells from the same animal species as the host. Hybrid monoclonal antibodies can be genetically engineered using human constant regions and mouse or rat variable regions as described by Morrison et al., *Proc. Natl. Acad. Sci. USA*, 81 (1984) 6851–6855. The antibodies may be one of the immunoglobulin classes (IgM, IgG, IgA, IgD, or IgE). Hence, the CD44 antibody utilized in this invention may be IM7 or a hybrid (rat/human) version of IM7 which has the same recognition site on CD44 as the original IM7 antibody.

PREPARATION OF ANTIBODY FORMULATION FOR DOSAGE

Antibody may be formulated with conventional pharmaceutically acceptable parenteral vehicles for administration by injection. Such vehicles are inherently nontoxic and nontherapeutic. Examples are water, saline, Ringer's solution, dextrose solution, and Hank's solution. The formulation may contain minor amounts of additives such as substances that maintain isotonicity, physiological pH (e.g., buffers) and stability (preservatives). The antibody is prepared in purified form substantially free of other proteins, endotoxins and other contaminants, and stored as a sterile, lyophilized (freeze-dried) powder. The antibody solution, free of aggregates, is formulated in sterile isotonic liquid at concentrations of about 1 to about 10 mg per ml and administered intravenously to patients during a period of several hours. Slow administration permits continuous monitoring of the vital functions of the patient. Experimental animals are also treated parenterally; intravenous administration can be used for larger animals and smaller ones can be injected intraperitoneally.

DOSAGE AND TREATMENT REGIMEN

The antibodies used in the method of the present invention are preferably administered to individuals, preferably mammals, more preferably humans, in a manner that will maximize the desired effect. Antibody may be administered prior to, or at the onset of, or during an acute (active) episode of an autoimmune inflammatory disease.

The dose for individuals of different species and for different diseases is determined by measuring the effect of the antibody on the lessening of those parameters which are indicative of the disease being treated. Being proteins, the antibodies will normally be administered parenterally, typically intravenously, as a bolus or in an intermittent or continuous regimen. The dose will depend upon the patient and the patients medical history.

For arthritis, local administration may be particularly effective, using means of subcutaneous implant, staples or slow release formulation implanted directly proximal the target. Slow-release forms can be formulated in polymers, such as Hydron (Langer, R., et al., *Nature*, 263 (1976) 797–799) or Elvax 40P (Dupont) (Murray, J. B. et al., In Vitro, 19 (1983) 743–747). Other sustained-release systems have been suggested by Hsieh, D. S. T., et al., *J. Pharm. Sci.*, 72 (1983) 17–22). Suitable pharmaceutical vehicles and their formulations are described in "Remington's Pharmaceutical Sciences" by E. W. Martin which is incorporated herein by reference.

In mouse models of rheumatoid arthritis, a single intraperitoneal or intravenous injection of 100 $\mu$g of IM7 antibody produced measurable reduction in joint swelling (FIG. 1). When mice were given 300 $\mu$g of antibody in two or more injections, swelling and inflammatory cell migration/accumulation was significantly reduced in every inflamed joint. A continuous regimen (daily injection of about 50 $\mu$g of antibody between days 1 and 10, and 100 $\mu$g total amount during days 11–14 in decreasing (40, 30, 20 and 10 $\mu$g) daily doses), resulted in nearly complete recovery of animals from arthritis and provided long-lasting remission. No further antibody injections were necessary to maintain the inflammation-free state in previously affected joints during a 60 day observation period. The total amount of antibody administered did not exceed 700 $\mu$g per animal.

Figure 2:
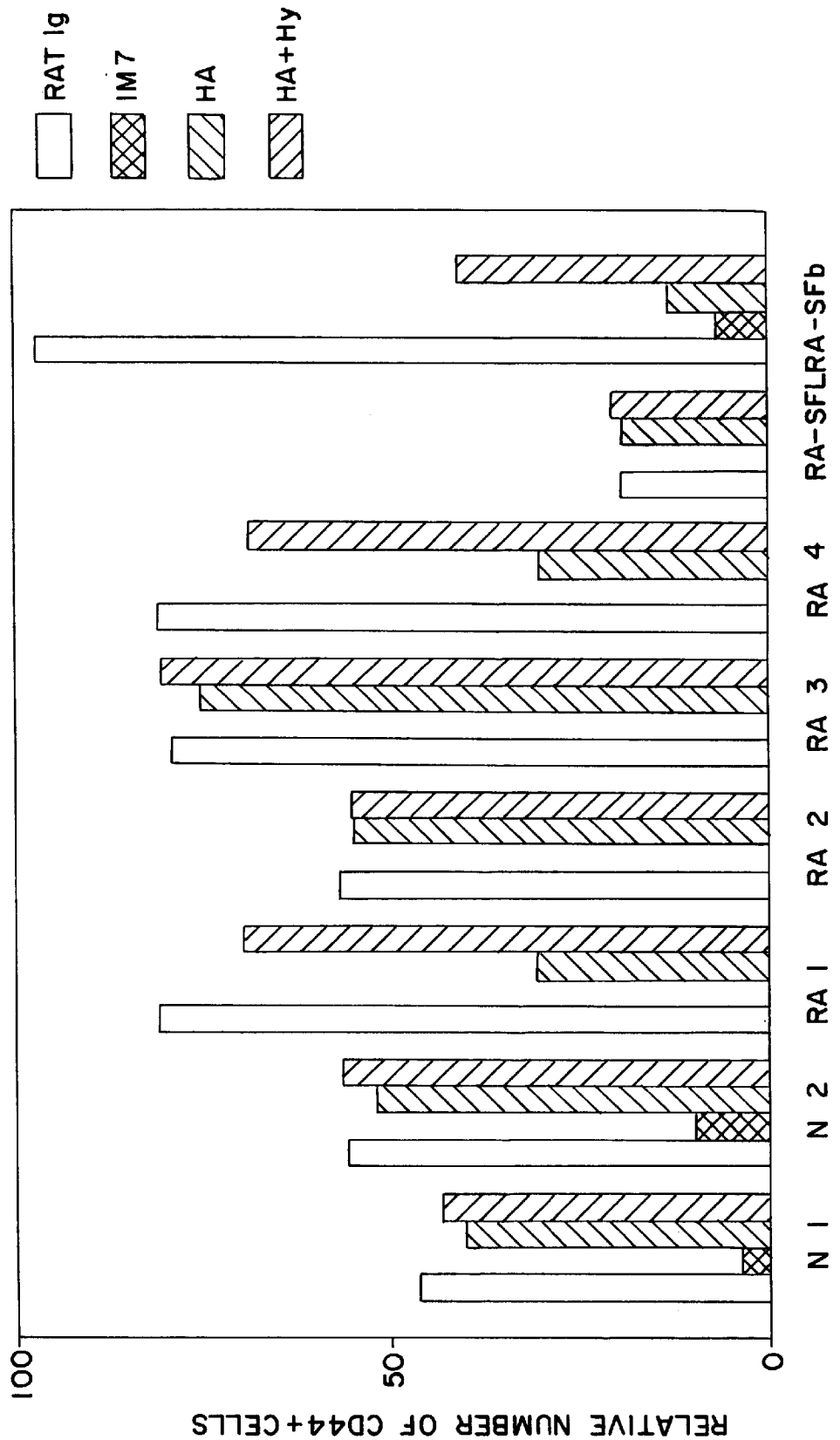
FIG. 2 illustrates that anti-CD44 mAb IM7 induces the shedding of CD44 from human leukocytes and synovial cells. Peripheral blood leukocytes (PBLs) from healthy donors (N) and from rheumatoid arthritis patients (RA), as well as RA synovial fluid leukocytes (SFL) and RA synovial fibroblasts (SFb) were treated with normal rat IgG (open bars), hyaluronan (HA) (hatched bars), hyaluronidase following HA treatment (HA+Hy) (dotted bars) or mAb IM7

Recent experimental observations (detailed in FIG. 2) indicate that antibody IM7 has the same effect on human cells in vitro as for the mouse system. Hence, dosage rates for humans can be extrapolated based on the results of animal data. For human use, for example in patients with rheumatoid arthritis, the patient is first given a single injection of IM7 antibody in a dosage ranging from about 5 to about 15 mg/kg, for a 70 kg average weight person, the dosage would be between about 350 and about 1050 mg per individual. In the event that this regimen does not produce the desired results, the patient is given the highest dose (15 mg/kg) divided in three consecutive daily injections. Effective treatment is reflected by clinical assessment (decrease in joint pain and swelling) and laboratory measurements (e.g., loss of CD44 from the surface of leukocytes and favorable change in serum markers of inflammation, e.g., a decrease in erythrocyte sedimentation rate (ESR), acute phase protein and circulating hyaluronan levels). The method of administering the dosage may be varied by the treating physician due to patient condition and the severity of the condition being treated.

While not intending to be bound by any theory, anti-CD44 treatment, especially with antibody IM7, has a two-fold effect exerted on both leukocytes and synovial cells. The antibody is able to interfere with the binding of hyaluronan by either synovial cell CD44 or leukocyte CD44 or both. Anti-CD44 antibodies provide their anti-inflammatory effect because they disrupt the sandwich interaction (i.e. hyaluronan sandwiched between synovial cell CD44 and leukocyte CD44) between CD44 and the hyaluronan rich extracellular matrix of inflamed tissue.

Binding of anti-CD44 antibody IM7 results in the loss of CD44 receptor from the surface of the cell. Binding of IM7 to CD44 activates proteolytic enzymes which remove the extracellular part of the receptor. The epitope to which IM7 binds is outside the hyaluronan binding domain of CD44. Pre-incubation of cells with hyaluronan does not inhibit the binding of IM7 to the receptor and vice versa, i.e., IM7 does not interfere directly with hyaluronan binding during a short-time incubation (30 min. to 1 hour). The loss of CD44-bound hyaluronan and further binding function of the receptor are a result of the removal of the hyaluronan-binding part of CD44 from the cell surface, which occurs in the continuous presence of antibody IM7 for more than 1 hour (usually 4–12 hours). Hence, anti-CD44 antibody does not merely block the receptor as do most antibodies used in immunotherapy, but induces the loss of CD44 receptor through shedding of the CD44 receptor, or in some cases, endocytosis and intracellular breakdown of CD44 together with receptor-bound hyaluronan. In synovial tissue, this results in the loss of CD44 bound hyaluronan and associated water from the tissue (decrease in swelling), and the loss of CD44 dependent migration of inflammatory cells into the tissue (decrease in leukocyte infiltration).

Many antibodies bind to their target receptor and remain on the cell surface for a period of time. Cells covered with receptor/antibody complexes frequently become a target for phagocytic or cytotoxic cells which are able to destroy them. Since anti-CD44 antibody IM7 induces the rapid loss of the receptor from the cell surface, the remaining antibody-free cell is not subjected to phagocytic and/or cytotoxic attacks, and as a result, further tissue destruction is prevented.

Treatment with CD44 antibodies provides an important benefit as in vivo and in vitro results in mice and in vitro data on human cells indicate that treatment with anti-CD44 antibody IM7 does not elicit profound changes in the original immune reactions. For example, circulating antibody levels and T lymphocyte reactions are the same in both IM7 treated and in nontreated arthritic mice; human and mouse lymphocyte response to recall antigens in vitro do not change significantly in the presence of antibody IM7 as illustrated in FIG. 3; and the levels of adhesion molecules, including L-selectin, LFA-1 and ICAM-1, or other cell surface antigens, do not show significant changes upon treatment with antibody IM7.

Anti-CD44 treatment with IM7 appears to be safer with regards to its effect on immune functions, than the administration of antibodies to other adhesion molecules as the mechanism of action of IM7 is different from that of other anti-adhesion antibodies. For example, anti-LFA-1 antibody M18 inhibits normal lymphocyte homing (to lymph nodes) in mice and interferes with antigen recognition by lymphocytes both in vivo and in vitro, while anti-CD44 antibody IM7 does not exhibit a detectable inhibitory effect on either lymphocyte homing to lymphoid organs or the function of the immune system.

In another aspect of the invention, the amino acid sequence of the binding site of antibody IM7 on CD44 has been identified. A synthetic CD44 peptide containing the binding site of IM7 is able to block the antibody in vitro and in vivo. Hence, should any imbalance (i.e. overdose, unexpected side effects, allergy) occur during the administration of IM7, this peptide can be utilized as an antidote to quickly neutralize the antibody and provide control over the effects of antibody IM7.

The following examples illustrate methods for carrying out the invention and should be understood to be illustrative of, but not limiting upon, the scope of the invention which is defined in the appended claims.

EXAMPLES

Example 1
Antibodies

Rat B-cell hybridomas that produce mAbs against murine CD44 (clones IM7.8.1 and KM 201) and CD18 (clone M18/2.a.12.7), as well as IgG2a (clone R17 217.1.3.) and IgG2b (clone M1/69.16.11.HL) mAbs to irrelevant murine antigens (transferring receptor and a heatstable antigen on red blood cells, respectively) were purchased from American Type Culture Collection (Rockville, Md.). Ascites fluids were generated in nude mice (Charles River Colony, Portage, Mich.). Monoclonal antibody IM7.8.1 (abbreviated as IM7) is a rat IgG2b raised against murine CD44 using a myeloid cell line form mouse bone marrow for the immunization of rats (Trowbridge et al., *Immunogenetics*, 15 (1982) 299–312). IM7 also recognizes human CD44 and binds to an epitope in the non-variable region of both human and mouse CD44 (Peach et al., *J. Cell Biol.*, 122 (1993) 257–264). A 13-amino acid-long sequence (NH2-Asp-Leu-Pro-Asn-Ser-Phe-Asp-Gly-Pro-Val-Thr-Ile-Thr-COOH) between residues 115 and 127 of murine CD44 is the putative IM7 epitope. KM201 (Miyake et al., *J. Exp. Med.*, 172 (1990) 69–75; Lesley et al., *J. Exp. Med.*, 175 (1992) 257–266) is a rat IgG1, which also binds to the non-variable region of murine CD44, but the epitope is located outside the binding site of IM7. Monoclonal antibody M18/2.a.12.7 (M18) is a rat IgG2a that recognizes the β-chain (CD18) of mouse LFA-1 and cross-reacts with the homologous monocyte/macrophage receptor Mac-1 (Sanchez-Madrid et al., *J. Exp. Med.*, 158 (1983) 586–6020). IgG fractions were purified from ascites fluids on a protein G column (Pierce, Rockford, Ill.). The purity of immunoglobulins (>95%) was determined by polyacrylamide gel electrophoresis. IgG contents were quantitated using a protein determination kit (Pierce) and by enzyme-linked immunosorbent assays using affinity-purified rat IgG1, IgG2a and IgG2b and mouse mAbs to rat IgG isotypes (PharMingen, San Diego, Calif.). IgG concentrations were adjusted to 1 mg ml$^{-1}$ in phosphate buffered saline (PBS), filtered through 0.22-$\mu$m pore sterile filters and stored at −20° C. Non-immune rat IgG was purchased from Sigma.

Example 2
Induction and Assessment of Proteoglycan and Collagen-Arthritis in Mice and Treatment with Antibodies BALB/c mice (Charles River, Portage, Mich.) were immunized with chondroitinase ABC-treated proteoglycans from canine articular cartilage as described previously (Glant et al., *Arthritis Rheum.*, 30 (1987) 201–212; Mikecz et al., *Arthritis Rheum.*, 37 (1994) 1595–1403). Age- and size-matched DBA/1 mice were immunized with type II collagen from chicken sternal cartilage as described (Courtenay et al., *Nature*, 282 (1980) 666–668; Williams et al., *J. Orthop. Res.*, 11 (1983) 172–180). Following the last antigen injection, the animals were examined daily for the onset of joint inflammation (swelling and erythema). Thickness of the ankle and wrist joints in both frontal and sagittal directions was measured using a microcaliper. Cumulative joint diameter (mm) was calculated for each mouse daily, before and during treatment with antibodies. Loss of joint function as a result of deformities was assessed by measuring the degree of extension in the ankle joints with a goniometer (Williams et al., *J. Orthop. Res.*, 11 (1983) 172–180). Mice that reached a 3-mm increase in cumulative joint thickness within 5 days following the onset of arthritis (Glant et al., *Arthritis Rheum.*, 30 (1987) 201–212); Mikecz et al., *Arthritis Rheum.*, 37 (1994) 1395–1403) were selected for antibody treatment. Animals with either proteoglycan- or collagen-induced arthritis were injected intraperitoneally with 100 $\mu$g of anti-CD44 antibody IM7 or anti-CD18 antibody M18 on day 0 of treatment. Purified rat IgG and rat mAbs to irrelevant mouse antigens were used as control immunoglobulins. Mice received 50 $\mu$g daily doses of antibodies between days 1 and 10. Between days 11 and 14, the animals were weaned off the therapy and killed on day 14. Some mice (not included in groups shown in FIG. 1) were killed on days 4 or 8 to assess joint inflammation histologically during antibody treatment.

Figure 1B:
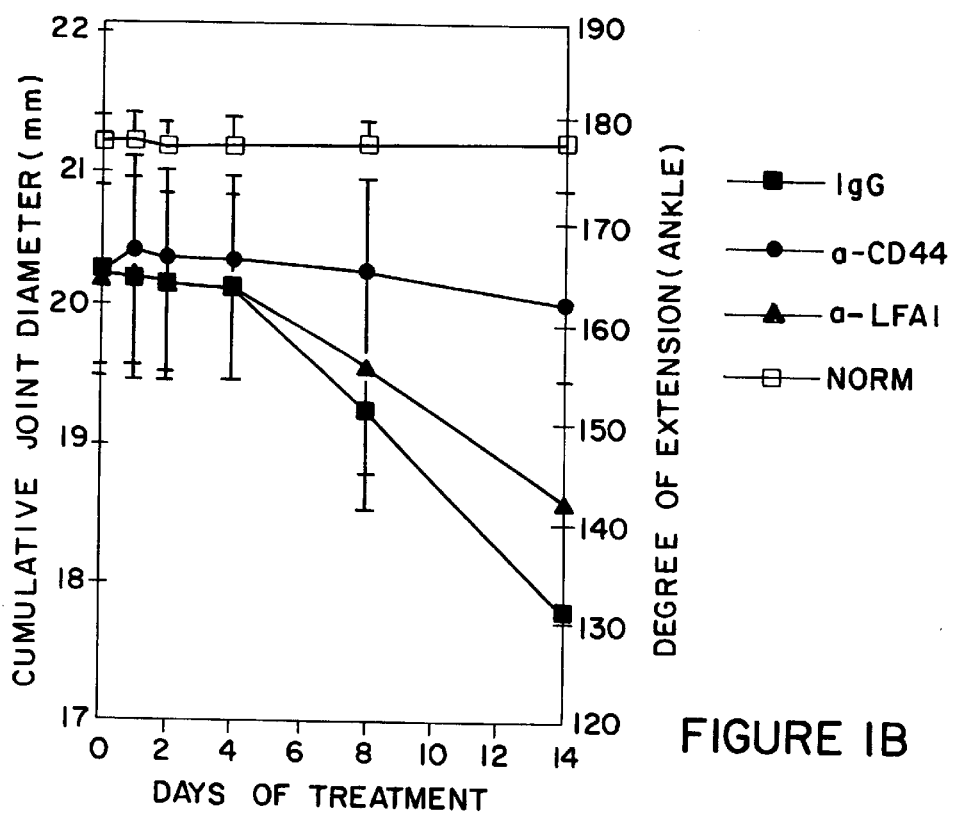

The intraperitoneal injection of anti-CD44 monoclonal antibody IM7 into mice with acute proteoglycan- or collagen-induced arthritis resulted in a striking reduction in joint swelling. A dramatic decrease in joint oedema was observed within 24–36 hours on each swollen limb following a single dose (100 μg) of the anti-CD44 antibody (FIG. 1a). Most of the animals treated daily with 50 μg of monoclonal antibody IM7 regained nearly normal joint function by day 8 (FIG. 1b). However, when anti-CD44 treatment was interrupted at that time, some symptoms of joint inflammation returned. When a continuous regimen of 50 μg antibody per day was used, no clinical relapses occurred during a 14-day treatment, and only mild synovitis recurred occasionally after the cessation of the therapy. Mice with either proteoglycan- or collagen-induced arthritis responded identically to anti-CD44 treatment, and no adverse effects were observed. Histopathology of the joints revealed a lack of leukocytes in the joint cavities and markedly reduced number of inflammatory cells in the synovial tissue on day 14. A moderate synovial hyperplasia, however, remained in IM7-treated animals as a consequence of the preceding inflammation.

The anti-CD18 antibody was chosen initially as a positive control because of its ability to bind to both mononuclear and polymorphonuclear leukocytes and its beneficial effect on experimentally induced arthritis (Sanchez-Madrid et al., *J. Exp. Med.*, 158 (1983) 586–602; Kakimoto et al., *Cell Immun.*, 142 (1992) 326–337). Treatment of arthritic mice with anti-CD18 monoclonal antibody M18 also resulted in a moderate clinical and histopathological improvement in each animal (less severe inflammation compared with mice injected with either nonspecific rat IgG or irrelevant monoclonal antibodies) (FIGS. 1a and b), but great variations were observed in joint thickness and histology from joint to joint. In contrast to IM7, the effect of monoclonal antibody M18 on joint swelling was not obvious before day 4 (FIG. 1a). The difference in the kinetics of the effects of anti-CD44 and anti-CD18 therapy, especially on joint oedema, suggested that the mechanisms of action of the two antibodies are different.

Example 3
Isolation of Leukocytes and Synovial Cells

Leukocytes (mononuclear and polymorphonuclear cells) were obtained from peripheral blood, spleens and lymph nodes of arthritic animals. Red blood cells were eliminated by hypotonic lysis. The number of viable leukocytes was determined by trypan blue exclusion and the ratios of cell types (lymphocytes, monocytes/macrophages and neutrophiils) by Giemsa staining. Synovial tissue was obtained from arthritic knee joints under a dissecting microscope. Synovial cells were liberated from the tissue by a 4-h digestion with bacterial collagenase (Worthington Biochemical Crop., Freehold, N.J.). Cells were cultured in Dulbecco's modified Eagle's medium (DMEM; Gibco, Grand Island, N.Y.) supplemented with 10% fetal bovine serum (FBS; Hyclone, Logan, Utah) and 50 μg ml$^{-1}$ gentamicin (Sigma). Adherent cells were detached by trypsinization and passaged three times to obtain predominantly fibroblast-type synovial cells.

Example 4
In Vivo Cell Migration

Leukocytes were collected from arthritic mice (not treated with antibodies) and labelled with PKH26-GL fluorescent cell linker (Sigma) as described previously (Mikecz et al., *Arthritis Rheum.*, 37 (1994) 1395–1403). Labelled cells (2×10$^7$ live cells per mouse) were injected intravenously into syngeneic arthritic animals undergoing treatment with either normal rat IgG or mAbs IM7 or M18 on day 1 of the experiment. Recipient mice were killed on day 4. Frozen sections were prepared from the forepaws and hindpaws, lungs, bone marrow, joint draining lymph nodes and Peyer's patches and examined using fluorescence microscopy (Mikecz et al., *Arthritis Rheum.*, 37 (1994) 1395–1403).

A large number of donor leukocytes appeared in the synovium of IgG-injected mice. Fluorescent cells failed to migrate into the synovial tissue of animals treated with either the anti-CD18 antibody M18 or the anti-CD44 antibody IM7. The absence of labelled leukocytes in the synovium could be attributed to the loss of adhesive function of CD18 and CD44 rather than a lack of inflammatory mediators and chemoattractants in situ, since these tissues were infiltrated with the hosts' own leukocytes which had been recruited at the onset of inflammation in all arthritic mice and persisted on day 4 of treatment. On the other hand, donor cells appeared in approximately equal numbers in both IgG- and IM7-treated mice when sections from lymphoid organs, bone marrow and lungs were compared. This observation indicated that the intrinsic motility and normal extravasation of these cells were not hampered by anti-CD44 treatment. Injection of recipient animals with monoclonal antibody M18, however, reduced the number of lymph node-homing leukocytes. These findings were in agreement with a recent study (Camp et al., *J. Exp. Med.*, 178 (1993) 497–507), which demonstrated that the lymph node-homing capacity of lymphocytes in mice did not change following in vivo anti-CD44 treatment but it was markedly reduced after injection with a monoclonal antibody against CD11a/CD18 (lymphocyte function-associated antigen type 1 (LFA-1) on lymphocytes). These results suggest that CD44, unlike LFA-1, is not necessary for normal lymphocyte homing.

Flow cytometric analysis (as described in Example 5) revealed a marked reduction of CD44 on leukocytes of animals treated with IM7 as compared with those injected with either rat IgG or the anti-CD18 antibody M18. The viability of cells and the ratio of various cell types (granulocytes, lymphocytes, monocytes/macrophages) were approximately the same in all animals, which indicates that the decrease of CD44 expression was not the result of a selective depletion of CD44 positive leukocytes.

Example 5
Fluorescence Flow Cytometry

Flow cytometric analysis was performed on the leukocytes of mice that underwent antibody treatment. CD44 expression on leukocytes from normal and arthritic but untreated animals after in vitro antibody treatment was also determined by flow cytometry. Cells were incubated with either IM7, KM201 or isotype-matched normal rat immunoglobulins. A biotinylated second antibody was used where indicated, followed by streptavidin-R-phycoerythrin. All incubations were carried out at 4° C. Immunostaining was analyzed on FACScan flow cytometer (Becton-Dickinson, Rutherford, N.J.) using Lysis II software (Brennan et al., *Clin. Exp. Immun.*, 100 (1995) 104–110; Buzas et al., *Cell Immun.*, 158 (1994) 292–304).

Example 6
In vitro Treatment of Leukocytes and Synovial Cells with Antibodies

Plastic 100-mm culture dishes (Corning Costar Corp., Cambridge, Mass.) were coated with nonimmune rat IgG or mAbs IM7 or M18 (500 μg antibody per dish in sterile sodium carbonate buffer, pH 9.6) overnight at 37° C. Non-specific binding sites were blocked with 1% FBS in DMEM. Leukocytes from arthritic mice were cultured in the IgG-coated dishes ($1 \times 10^7$ cells per dish in DMEM containing 5% FBS) for 12 hours. In some experiments, leukocytes were incubated in the antibody-coated dishes in the presence of various protease inhibitors (Bazil et al., *J. Immun.*, 149 (1992) 147–753; Glant et al., *Biochem. J.*, 234 (1986) 31–41; Brennan et al., *Clin. Exp. Immun.*, 100 (1995) 104–110), including 1–5 mM phenylmethylsulfonyl fluoride (PMSF, Sigma) or 0.1–1.0 U ml$^{-1}$ aprotinin (Calbiochem, La Jolla, Calif.). Cells were collected, washed and the number of viable cells was determined by trypan blue exclusion. Synovial cells ($1 \times 10^4$) were detached from culture dishes using a non-enzymatic cell dissociation solution (Sigma) and transferred to tissue culture chamber slides (Nunc Inc., Naperville, Ill.) coated previously with mAbs IM7 or M18 or rat IgG. Direct immunofluorescence staining was carried out after a 12-hour incubation using biotinylated mAbs IM7 or M18 (PharMingen) and R-phycoerythrin-conjugated streptavidin (Gibco). Purified mAb KM201 and biotinylated goat anti-rat IgG (PharMingen) were used for indirect immunostaining. Using this method, both IM7 and KM201, bound to the cell surface, were detected by the anit-rat antibody, reflecting the total amount of CD44 receptors present on the cell.

IM7, but neither normal rat IgG nor antibody M18, significantly reduced the expression of CD44 on the surface of leukocytes within 12–20 hours. The most extensive loss of CD44 occurred when leukocytes were exposed to IM7 immobilized to plastic. Synovial cells also lost CD44 expression during a 12-hour culture in IM7-coated dishes.

Example 7

Hyaluronan Binding (particle exclusion) Assay

Synovial cells were seeded into 35-mm culture dishes previously coated with either rat IgG or antibody IM7. Alternatively, synovial cells were cultured overnight in non-coated dishes in the presence of various amounts (50–150 μg ml$^{-1}$) of antibodies added to the culture medium. Endogenously produced hyaluronan was removed with protease-free Streptomyces hyaluronidase (Sigma) before the assay (Knudson, *J. Cell Biol.*, 120 (1993) 825–834). The ability of the cells to assemble a hyaluronan-rich pericellular matrix was tested by the addition of exogenous high molecular weight hyaluronan from human umbilical cord (Sigma) and proteoglycan (aggrecan) monomers purified from rat chondrosarcoma, as described (Knudson, *J. Cell Biol.*, 120 (1993) 825–834; Glant et al., *Biochem J.*, 234 1986) 31–41). The pericellular matrix was visualized by exclusion of particles (paraformaldehyde-fixed red blood cells) (Knudson, *J. Cell Biol.*, 120 (1993) 825–834). Hyaluronidase sensitivity (hyaluronan content) of the matrix was assessed by subsequent digestion with Streptomyces hyaluronidase (Toole, *Cell Biology of Extracellular Matrix*, Plenum, N.Y. (1991) 305–341; Knudson, *J. Cell Biol.*, 120 (1993) 825–834)

Synovial cells elaborated a prominent pericellular matrix upon addition of hyaluronan (Knudson, *J. Cell Biol.*, 120 (1993) 825–834) in the presence or absence of rat IgG or monoclonal antibody M18. This matrix was eliminated by hyaluronidase treatment, and it could not develop around IM7-treated synovial cells, suggesting that hyaluronan molecules were anchored to the cell membrane primarily via CD44.

Example 8

Western Blot Analysis of Soluble CD44 in Mouse Sera

Sera collected from IM7-, M18- or non-immune rat IgG-treated mice were immunosorbed onto an anti-rat IgG-Sepharose 4B (Sigma) column and the proteins eluted with 3 M KSCN. Samples were dialysed, lyophilized, redissolved in 10 μl loading buffer and boiled for 5 minutes. Electrophoresis was performed in a 7.5% polyacrylamide gel in the presence of 0.1% SDS. Proteins were transferred onto a nitrocellulose membrane and probed with either biotinylated IM7 or M18, followed by peroxidase-conjugated streptavidin, chromogen and substrate, respectively. The reaction was visualized by the enhanced chemiluminescence (ECL; Amersham Corp., Arlington Heights, Ill.) method (Cs-Szabo et al., *Arthritis Rheum.*, 38 (1995) 660–668). To obtain "free" CD44 (not complexed with antibodies), separate aliquots of serum samples were absorbed onto mAb IM7 coupled to CNBr-activated Sepharose CL4B (Glant, *Biochem. Biophys. Res. Commun.*, 106 (1982) 158–163), and the eluted proteins were subjected to immunoblotting as described above.

There was no detectable loss of CD44 from IM7-treated cells in the presence of serine protease inhibitors in vitro. This indicated that the antibody-induced loss of CD44 in vivo might be the result of enzymatic cleavage of the extracellular domains of the receptor. These observations are consistent with results from other studies that have demonstrated shedding of CD44 from murine lymphocytes (Camp et al., *J. Exp. Med.*, 178 (1993) 497–507) or human leukocytes (Bazil et al., *J. Immun.*, 149 (1992) 747–753) exposed to anti-CD44 antibodies.

One dominant species of CD44 cleavage products was detected in the sera of rat IgG-treated or untreated arthritic mice, whereas multiple fragments were recovered from the sera of arthritic animals injected with anti-CD44 antibody. Two fragments with apparent molecular masses of 68 and 102 kD, corresponded to the sizes of CD44 identified in normal human sera (Bazil et al., *J. Immun.*, 149 (1992) 747–753). The multiple protein bands may represent different splice variants or degradation products or differentially glycosylated forms of the shed CD44.

Example 9

Statistical Analysis

A Repeated Measures Analysis of Variance was conducted using SAS System software (SAS Institute, *SAS User's Guide*, SAS Institute, Cary, N.C. (1985) 113–137). Post hoc analyses used the Ryan-Einot-Gabriel-Welsch multiple range test available in the SAS software. This test was chosen as it controls the experimentwise type I error rate at the selected ($P<0.05$) level.

Numerous modifications and variations in practice of the invention are expected to occur to those skilled in the art upon consideration of the foregoing detailed description of the invention. Consequently, such modifications and variations are intended to be included within the scope of the following claims.

What is claimed is:

1. A method for inhibiting tissue destruction associated with autoimmune inflammatory diseases, the method comprising administering an effective amount of an antibody which binds to CD44 on synovial cells and on leukocytes and inhibits leukocyte infiltration into synovial tissues;

where said antibody prevents binding of CD44 on synovial cells and leukocytes to hyaluronan by inducing loss of said CD44 from synovial cells and leukocytes, the antibody binding to CD44 outside of a hyaluronan binding domain of CD44; and where the binding of said antibody does not interfere directly between the binding of CD44 with hyaluronan.

2. The method of claim 1 wherein the antibody which binds to CD44 on synovial cells and on leukocytes is a monoclonal antibody.

3. The method of claim 1 wherein the antibody which binds to CD44 on synovial cells and on leukocytes is accession number ATCC TIB 235 or an antibody which has the same recognition site on CD44 as accession number ATCC TIB 235.

4. The method of claim 1 wherein the administration of antibody which binds to CD44 on synovial cells and on leukocytes results in reduced tissue swelling and leukocyte accumulation in inflamed tissues.

5. The method of claim 1 wherein a therapeutically effective amount of antibody which binds to CD44 on synovial cells and on leukocytes is administered in a pharmacologically acceptable carrier.

6. The method of claim 5 wherein the pharmacologically acceptable formulation is administered intravenously at selected time periods prior to or during the onset or during an acute episode of the autoimmune inflammatory disease.

7. The method of claim 5 wherein the pharmacologically acceptable formulation is administered locally to a joint.

8. A method for inhibiting tissue destruction associated with autoimmune inflammatory diseases in humans or in animals, the method comprising administering in vivo antibody which binds to CD44 on synovial cells and on leukocytes in an amount effective for inducing loss of CD44 from synovial cells and leukocytes, preventing accumulation of CD44-bound hyaluronan associated water in tissue, and causing leukocytes to lose their ability to migrate into inflamed tissue, the antibody binding to CD44 outside of a hyaluronan binding domain of CD44.

* * * * *

UNITED STATES PATENT AND TRADEMARK OFFICE
CERTIFICATE OF CORRECTION

PATENT NO. : 6,001,356
DATED : December 14, 1999
INVENTOR(S) : Mikecz et al.

It is certified that error appears in the above-identified patent and that said Letters Patent is hereby corrected as shown below:

Column 1,
Line 4, please insert the following paragraph after the Title:

-- STATEMENT OF GOVERNMENT RIGHTS
 The U.S. Government has a paid-up license in this invention and the right in limited circumstances to require the patent owner to license others on reasonable terms as provided for by the terms of Grant No. AR40310 awarded by the National Institutes of Health. --

Signed and Sealed this

Twenty-ninth Day of June, 2004

JON W. DUDAS
*Acting Director of the United States Patent and Trademark Office*